United States Patent [19]

Blank et al.

[11] Patent Number: 4,814,483

[45] Date of Patent: Mar. 21, 1989

[54] PROCESS FOR THE PREPARATION OF OPTIONALLY SUBSTITUTED 2-BENZYL-TOLUENES

[75] Inventors: Heinz U. Blank, Odenthal; Gunter Silber, Cologne, both of Fed. Rep. of Germany

[73] Assignee: Bayer Aktiengesellschaft, Leverkusen, Fed. Rep. of Germany

[21] Appl. No.: 941,017

[22] Filed: Dec. 12, 1986

[30] Foreign Application Priority Data

Dec. 18, 1985 [DE]  Fed. Rep. of Germany ....... 3544733

[51] Int. Cl.[4] .................. C07C 121/60; C07C 121/66; C07C 121/62
[52] U.S. Cl. ..................................... 558/411; 558/413; 558/414; 558/424; 558/425; 568/34; 568/635; 568/928; 570/184; 585/462; 564/181; 564/221
[58] Field of Search ....................... 585/462; 570/184; 558/411; 568/34, 635

[56] References Cited

U.S. PATENT DOCUMENTS 2,403,748  7/1946  Olin ................................. 585/462 X
3,739,040  6/1973  Boggs ............................. 585/462 X

FOREIGN PATENT DOCUMENTS 2840272  4/1979  Fed. Rep. of Germany .

OTHER PUBLICATIONS

Patent Abstracts of Japan, unexamined application, Feld C, Band 9, Nr. 317, 12. Dec. 1985 The Patent Office Japanese Government Seite 64 C 319 *Zusammenfassung Nr. 60-152 429 (Suketaka Harada).
The Journal of Organic Chemistry, Band 43, 1978 M. Tashiro et al. "Studies on selective preparation of aromatic compounds.15, The Lewis acid catalyzed transalkylation of some tert-butyl-diphenylmethanes and -ethanes in aromatic solvents" Seiten 1413–1420.
Organic Preparation and Procedures International, Band 10, Feb. 1978 V. Bohmer et al. "The t-butyl group as a possible protective group in the synthesis of oligo (hydroxy-1,3-phenylene)methylenes" Seiten 113–121.
Synthesis, 1979, Nr. 12, Dec. 1979 M. Tashiro "Selective synthesis of aromatic compounds using positional protective groups" Seiten 921–936.
Houben Weyl "Methoden der organischen Chemie", 4. Auflage, Band V/2b "Arene, Arine" 1981 Georg Thieme Verlag, Stuttgart Seiten 238–254.

Primary Examiner—Joseph Paul Brust
Attorney, Agent, or Firm—Sprung Horn Kramer & Woods

[57]  ABSTRACT

Optionally substituted 2-benzyl-toluenes can be prepared by reaction of optionally substituted 2-benzyl-tert.-alkyl-toluenes with an optionally substituted aromatic hydrocarbon in the presence of anhydrous iron-(III) halide. The reaction is carried out at ambient to elevated temperature. The optionally substituted aromatic hydrocarbon is employed in molar excess, relative to the 2-benzly-tert.-alkyl-toluenes.

12 Claims, No Drawings

PROCESS FOR THE PREPARATION OF OPTIONALLY SUBSTITUTED 2-BENZYL-TOLUENES

The present invention relates to a process for the preparation of optionally substituted 2-benzyl-toluenes by reaction of optionally substituted 2-benzyl-tert.-alkyl-toluenes with an optionally substituted hydrocarbon in the presence of anhydrous iron-(III) halide.

Several processes are known for the preparation of 2-benzyl-toluenes, thus, for example, the alkylation of toluene using benzyl chloride in the presence of zinc dust (Chem. Ber. 6 (1873), p. 907 et. seq.) or in the presence of beryllium chloride (Chem. Ber. 72 (1939), p. 1,414 et. seq.). However, difficult-to-separate mixtures comprising mainly 2- and 4-benzyl-toluene are produced which make this process unsuitable for industrial use.

Another process comprises the alkylation of aromatic hydrocarbons using 2-methyl-benzyl chloride in the presence of sulphuric acid, phosphoric acid or $BF_3$ (DE-OS (German Published Specification) No. 2,408,529, DE-OS (German Published Specification) No. 2,456,747, EP-OS (European Published Specification) No. 37,628, and DE-OS (German Published Specification) No. 2,336,289). However, these processes also only lead to uniform products when 2-methyl-benzyl chloride is reacted either with unsubstituted benzene or with symmetrically disubstituted benzenes. In contrast, benzene derivatives which are otherwise substituted produce isomeric mixtures which are difficult to separate.

It is additionally known that, in some cases with tert.-alkyl groups such as the tert.-butyl or the tert.-amyl group, individual positions on the aromatic systems can be protected against attack by electrophilic agents (Houben-Weyl vol. 5/2b (1981), p. 238; Synthesis 1979 p. 921). The protecting group is cleaved off again by transalkylation onto another aromatic system, for example using Friedel-Crafts catalysts, after carrying out the electrophilic reaction.

However, this procedure cannot be employed for the preparation of uniformly substituted diphenylmethanes since the cleavage of the benzyl bridge competes with the elimination of the protecting group (Houben-Weyl loc. cit.). The elimination of the tert.-butyl protecting group from the correspondingly substituted starting materials in the presence of the mildly reacting aluminum chloride/nitromethane complex only succeeds in the special case of 2,2'-dihydroxy-diphenylmethanes, whereas, under the same conditions, the protecting groups could only be removed from 4,4'-dihydroxy-diphenylmethanes with simultaneously proceeding transbenzylation. The special status of diphenylmethanes which carry hydroxyl substituents in the ortho position to the methylene group is also confirmed in Org. Prep. Proc. Int. 10 (1978), p. 113. In this case, the elimination of the protecting groups succeeded using 1.25 equivalents of $AlCl_3$, relative to the diphenylmethane compound, in toluene, whereas the elimination of tert.-butyl protecting groups from diphenylmethanes without hydroxyl groups leads, as a rule, to complex reaction mixtures. Besides the aluminum chloride/nitromethane complex mentioned, other typical Friedel-Crafts catalysts, such as, for example, $TiCl_4$ or $SnCl_4$, also produced undesired by-products from the transfer of benzyl groups. Absolutely no reaction could be obtained in a series of diphenylmethane derivatives using $TiCl_{14}$ or $SnCl_{14}$. The tert.-butyl groups could only be eliminated selectively, using aluminum chloride/nitromethane, from 4,4'-bis-tert.-butyl-diphenylmethane (J. Org. Chem. 43 (1978), p. 1,413).

Surprisingly, it has now been found that optionally substituted 2-benzyl-tert.-alkyl-toluenes can be reacted with an optionally substituted aromatic hydrocarbon in the presence of anhydrous iron-(III) halide to form optionally substituted 2-benzyl-toluenes.

Accordingly, a process for the preparation of 2-benzyl-toluenes of the formula

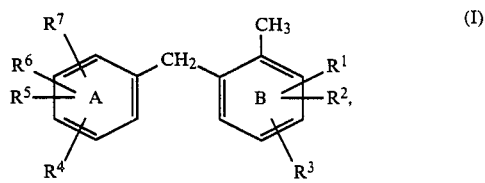

in which $R^1$ to $R^7$, independently of one another, denote hydrogen, halogen, alkyl, aryl, nitro, cyano, acylamino, aryloxy, arylsulphonyl or alkylsulphonyl, where in nucleus B, either the para position to the methyl group or the para position to the methylene group is unsubstituted and where each two of the radicals $R^1$–$R^7$, when they are neighboring, can form fused aromatic or cycloaliphatic ring, has been found which is characterized in that 2-benzyl-tert.-alkyl-toluenes of the formula

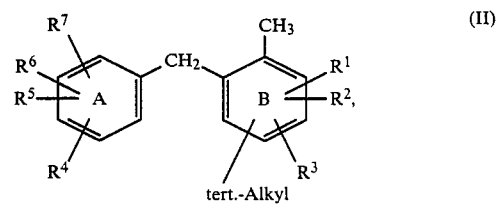

in which $R^1$ to $R^7$ have the meaning mentioned and the tert.-alkyl group is in the para position to the methyl group or in the para position to the methylene group, are reacted with an excess of an aromatic hydrocarbon of the formula

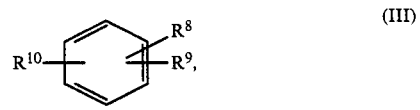

in which $R^8$ to $R^{10}$, independently of one another, denote hydrogen, alkyl or aryl, where two of the radicals $R^8$–$R^{10}$, when they are neighboring, can form fused aromatic or cycloaliphatic ring, in the presence of anhydrous Fe-(III) halide.

Fluorine, chlorine, bromine and iodine, preferably fluorine, chlorine and bromine, particularly preferably chlorine or bromine, may be mentioned as examples of halogen.

Alkyl having 1–10 C-atoms, preferably 1–6 C-atoms, particularly 1–4 C-atoms, such as methyl, ethyl, propyl, butyl, hexyl, octyl and decyl may be mentioned as alkyl. Methyl or ethyl may be mentioned in a very particularly preferred fashion. Alkyl carries at most one branch on the α-C-atom, preferably no branch on the α-C- atom, and particularly preferably also no branch on the further C-atoms.

Phenyl, naphthyl, anthryl, phenanthryl or diphenylyl, preferably phenyl or naphthyl, particularly preferably phenyl, may be mentioned as examples of aryl. Such aryl radicals can themselves be substituted by alkyl or halogen.

Two of the radicals $R^1$ to $R^7$, when they are neighboring, can, furthermore, form a fused aromatic or cycloaliphatic ring. The aromatic nucleus A (I) can carry one or two such fused rings. In the case of a fused aromatic ring, the aromatic nucleus A and/or B becomes, for example, the naphthalene system, and in the case of 2-fold fusion, the aromatic nucleus A also becomes the anthracene or the phenanthrene system. In the case of a fused cycloaliphatic ring the indane, the tetraline, the benzo-cycloheptyl or the benzo-cyclooctyl system is produced in a corresponding fashion.

Substituents of the formulae —NHCO-alkyl or —NHCO-aryl in which alkyl and aryl have the abovementioned meaning may be mentioned as examples of acylamino. Alkyl and aryl in the aryloxy, arylsulphonyl and alkylsulphonyl substituents likewise have the abovementioned meaning.

Tertiary alkyl groups which have 4–8 C-atoms and in which the α-C-atom is a tertiary C-atom, for example tert.-butyl, tert.-amyl, tert.-hexyl or tert.-octyl, may be mentioned as tertiary alkyl groups. The tert.-butyl group may be mentioned in a preferred fashion.

The tert.-alkyl group is either in the para position to the methyl group or in the para position to the methylene group.

In the process according to the invention, 2-benzyl-tert.-alkyl-toluenes of the formula

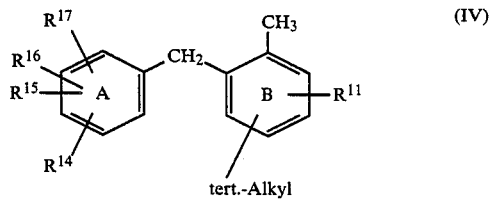

are preferably employed in which $R^{11}$, and $R^{14}$ to $R^{17}$, independently of one another, denote hydrogen, fluorine, chlorine, bromine, nitro, alkyl or phenyl, where two of the radicals $R^{14}$–$R^{17}$, when they are neighboring, can form a fused aromatic or cycloaliphatic ring and the tert.-alkyl group is in the para position to the methyl group or in the para position to the methylene group.

2-Benzyl-tert.-alkyl-toluenes of the formula

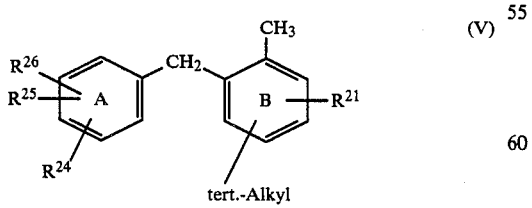

in which
$R^{21}$ denotes hydrogen or alkyl, and
$R^{24}$–$R^{26}$ have the range of meanings mentioned for $R^{14}$ to $R^{17}$ in (IV) and the tert.-alkyl group occupies the postion mentioned in (IV), are employed in a particularly preferred fashion.

2-Benzyl-tert.-alkyl-toluenes of the formula

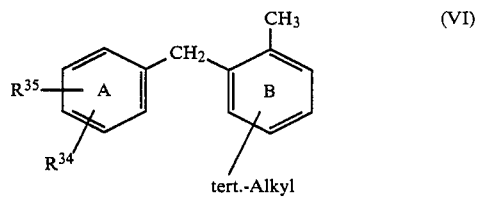

in which $R^{34}$ and $R^{35}$ have the range of meanings stated for $R^{14}$–$R^{17}$ in (IV) and the tert.-alkyl group occupies the position mentioned in (IV), are employed in a very particularly preferred fashion.

Examples of 2-benzyl-tert.-alkyl-toluenes which can be employed in the process according to the invention are: 2-benzyl-4-tert.-butyl-toluene, 2-benzyl-5-tert.-butyltoluene, 2-(2-chlorobenzyl)-4- or -5-tert.-butyltoluene, 2-(3-chlorobenzyl)-4- or -5-tert.-butyl-toluene, 2-(4-chlorobenzyl)-4- or -5-tert.-butyl-toluene, 2-(2,3-dichlorobenzyl)-4- or -5-tert.-butyl-toluene, 2-(2,4-dichlorobenzyl)-4- or -5-tert.-butyl-toluene, 2-(2,5-dichlorobenzyl)-4- or -5-tert.-butyl-toluene, 2-(3,4-dichlorobenzyl)-4- or -5-tert.-butyl-toluene, 2-(2-fluorobenzyl)-4- or -5-tert.-butyl-toluene, 2-(3-fluorobenzyl)-4- or -5-tert.-butyl-toluene, 2-(4-fluorobenzyl)-4- or -5-tert.-butyl-toluene, 2-(2-bromobenzyl)-4- or -5-tert.-butyl-toluene, 2-(3-bromobenzyl)-4- or -5-tert.-butyl-toluene, 2-(4-bromobenzyl)-4- or -5-tert.-butyl-toluene, 2-(2-nitrobenzyl)-4- or -5-tert.-butyl-toluene, 2-(3-nitrobenzyl)-4- or -5-tert.-butyl-toluene, 2-(4-nitro-benzyl-4- or -5-tert.-butyl-toluene, 2-(2-methylbenzyl)-4- or -5-tert.-butyl-toluene, 2-(3-methyl-benzyl)-4- or -5-tert.-butyl-toluene, and 2-(4-methyl-benzyl)-4- or -5-tert.-butyl-toluene.

According to the invention, an aromatic hydrocarbon of the formula

in which $R^{18}$ and $R^{19}$ have the range of meanings stated for $R^8$–$R^{10}$ in (III) are employed in a preferred fashion as aromatic hydrocarbon.

An aromatic hydrocarbon of the formula

in which $R^{28}$ and $R^{29}$, independently of one another, denote hydrogen, methyl, ethyl or phenyl, is employed in a particularly preferred fashion.

Examples of aromatic hydrocarbons for the process according to the invention are: benzene, toluene, o-, m- and p-xylene, 1,2,4-trimethylbenzene, 1,2,3,4-tetramethylbenzene, ethylbenzene, o-, m- and p-ethyl-toluene, o-, m- and p-diethylbenzene, n-propyl-benzene, o-, m- and p-(n-propyl)-toluene, n-butylbenzene, tetralin, napthalene, 1- and 2-methyl-naphthalene, 1- and 2-ethyl-naphthalene, 1- and 2-phenyl-naphthalene, diphenyl, and 1-, 2- and 3-methyldiphenyl. Benzene or toluene is employed as aromatic hdyrocarbon in a very particularly preferred fashion.

The aromatic hydrocarbon is employed in excess, relative to the 2-benzyl-tert.-alkyl-toluene, for example in an amount of 1-20 mol, preferably 2-15 mol, particularly preferably 4-12 mol, per mol of 2-benzyl-tert.-alkyl-toluene. The use of more than 20 mol of the aromatic hydrocarbon is possible in principle, but brings no further advantages. Of course, mixtures of the aromatic hydrocarbons mentioned can also be employed in the process according to the invention. Moreover, additional inert solvents can be employed in the process according to the invention. Such additional solvents must be inert towards the other reaction participants under the conditions of the process according to the invention, for example aliphatic hydrocarbons, such as hexane, heptane, and octane, benzine fractions, halogenated aliphatic hydrocarbons, such as methylene chloride and tetrachloroethane, halogenated aromatic hydrocarbons having two or more halogen atoms, such as dichlorobenzene, dibromobenzene and trichlorobenzene, or nitrobenzene.

The process according to the invention is carried out in the presence of anhydrous Fe-(III) halide, for example $FeCl_3$ or $FeBr_3$ or a mixture of the two, preferably in the presence of $FeCl_3$. The amount of Fe-(III) halide is, for example, 0.05-1 mol, preferably 0.2-0.8 mol, particularly preferably 0.2-0.6 mol, per mol of 2-benzyl-tert.-alkyl-toluene. The use of more than 1 mol of Fe-(III) halide is possible in principle, but brings no further advantage.

The process according to the invention is carried out at a temperature of 0°-150° C., preferably 0°-100° C., particularly preferably 5°-80° C. The choice of temperature depends on the amount of catalyst employed. Thus, it is advantageous, for example, to add more catalyst at higher temperatures in order to achieve a substantially quantitative elimination of the tert. butyl group. On the other hand, less catalyst can be used in an advantageous manner at lower temperatures. The process can be carried out at atmospheric pressure, increased pressure or reduced pressure. An increased pressure is applied, for example, in order to keep low-boiling reaction components in the liquid phase at the selected reaction temperature. The process is carried out at atmospheric pressure in preferred fashion.

The reaction components can be mixed in any sequence, in principle. For example, all reaction components can be initially introduced at room temperature and the reaction mixture brought to the desired temperature. A further procedure comprises initially introducing the iron-(III) halide into the total amount of aromatic hydrocarbon provided and heating to the reaction temperature and subsequently metering in the 2-benzyl-tert.-alkyl-toluene. Alternatively, a part of the aromatic hydrocarbon can also serve as solvent for the 2-benzyl-tert.-alkyl-toluene.

The reaction time is dependent on the molar amount of iron-(III) halide employed and the selected reaction temperature. The end of the reaction can be determined, for example, in a fashion familiar to the expert by chromatographical examination of samples removed from the reaction mixture. A short post-reaction time can be added before the work-up.

For work-up of the reaction mixture, the iron(III) halide can be hydrolyzed, for example, by addition of water or dilute mineral acid at 0°-100° C. The aqueous/organic mixture produced can be subjected to clarification by filtration, if this is desired, before the phase separation. For this purpose, for example, the mixture can be filtered through conventional acid-stable filters, if appropriate after addition of commercially available clarification and/or filtration auxiliaries, such as cellulose powders, Tonsil, activated charcoal and/or kieselguhr. After the phase separation, the organic phase is conventionally washed with water and/or 1-10% by weight strength sodium bicarbonate solution. The organic phase is further worked-up by conventional methods, for example by distillation or crystallization. During the distillation, the first fraction produced is, in general, the excess of the aromatic hydrocarbon employed; this can be reused in the process according to the invention after drying. The tert.-alkyl group-substituted aromatic hydrocarbon and the 2-benzyl-toluene which is the product according to the invention can be isolated as further fractions by precision distillation, if appropriate in vacuo, or by fractional crystallization.

In a further form of work-up of the reaction mixture from the process according to the invention, this reaction mixture, without addition of water or dilute mineral acid, is separated from undissolved iron-(III) halide by filtration. The filtrate is then worked-up by distillation, during which the recovered excess of the aromatic hydrocarbon is produced in anhydrous form and can be employed in the process according to the invention without further preparation.

The 2-benzyl-tert.-alkyl-toluenes employed according to the invention are known compounds or can be prepared by known methods (DE-OS (German Published Specification) No. 2,840,272; Zh. Org. Khim. 19 (1983), p. 1,674 in the original publication or p. 1,484 in the English translation). Thus, for example, p-tert.-butyl-toluene can be reacted with optionally substituted benzyl halides in the presence of Friedel-Crafts catalysts, such as $AlCl_3$, $FeCl_3$ or $TiCl_{14}$, and, if appropriate, in inert solvents in a fashion which is known per se.

In a further form of the process according to the invention, the reaction of a benzyl halide of the formula

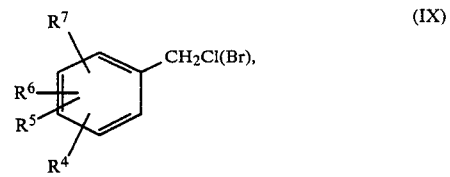

(IX)

in which $R^4$ to $R^7$ have the abovementioned meaning, with a tert.-alkyl-toluene of the formula

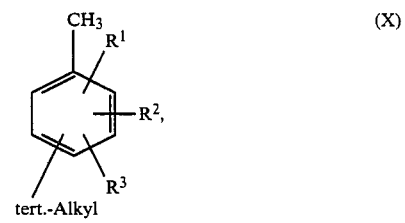

(X)

in which $R^1$ to $R^3$ have the abovementioned meaning, an ortho position to the methyl group is free and the tert.-alkyl group is in the para position to the methyl group or to the free ortho position mentioned, is carried out, as a first stage in the overall process, at elevated temperature, for example 80°–200° C., preferably 100°–150° C., and in the presence of iron-(III) halide.

In this case, (X) is employed in excess, for example in an amount of 2–20 mol, preferably 5–15 mol, particularly preferably 5–10 mol, per mol of (IX). The iron-(III) halide is employed, for example, in an amount of 0.01–0.5 mol, preferably 0.01–0.1 mol per mol of (IX).

After the completion of the first reaction stage described, the excess (X) is removed by distillation and can be fed back again to the first stage without further purification. An aromatic hydrocarbon (III) can be added, according to the invention, to the residue, in the form described above, of this first reaction stage, any deficiency of iron-(III) halide is replenished by further addition of iron-(III) halide, and the second stage is carried out in the sense described above.

However, it is, in principle, also possible to leave the excess of the tert.-alkyl-toluene (X) in the reaction mixture from the first stage described and to carry out the second stage after addition of the aromatic hydrocarbon. However, it is preferable to remove the excess of (X) by distillation before carrying out the second stage.

In a further form of the process according to the invention, it has been shown that it is advantageous to employ a toluene of the formula

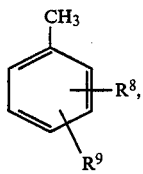
(XI)

in which $R^8$ and $R^9$, independently of one another, denote hydrogen, alkyl or aryl and, in the case where they are neighboring, can also form a fused aromatic or cycloaliphatic ring and in which one of the ortho positions to the methyl group is free and the para position to the methyl group or to the free ortho position mentioned is likewise free, as aromatic hydrocarbon from which a tert.-alkyl-toluene of the formula

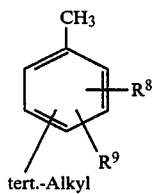
(XII)

in which $R^8$ and $R^9$ have the abovementioned meaning and in which one of the ortho positions to the methyl group is free and the tert.-alkyl group is in the para position to the methyl group or to the free ortho position mentioned, is produced in the course of the reaction.

This substituted tert.-alkyl-toluene of the formula (XII) can then be isolated, as was described above, and re-reacted with a benzyl halide (IX) in the first stage described above.

In the course of the further examination of the process according to the invention in its two-stage version, as described above, it has been shown that, when substituted toluenes (XI) are used, mainly tert.-alkyl-toluenes (XII) are produced in which the tert.-alkyl group is in the para position to the methyl group, so long as the para position is free. However, the para-substituted (XII) partially isomerizes during the reaction and any added post-reaction time to form the meta-isomers, so long as one of the meta positions to the methyl group is free. Now, it was extremely surprising that mixtures of the tert.-alkyl-toluenes (XII) in which the tert.-alkyl group and the methyl group occur adjacently in the para and meta positions and which have a free ortho position to the methyl group, which is simultaneously in the para position to the meta tert.-alkyl group mentioned, are also recycled without loss of selectivity, that is to say can be reacted with a benzyl halide (IX) to form the starting material of the 2-benzyl-tert.-alkyl-toluene to be employed according to the invention. This is the case, for example, when the aromatic hydrocarbon (XI) is the unsubstituted toluene or a toluene of the formula

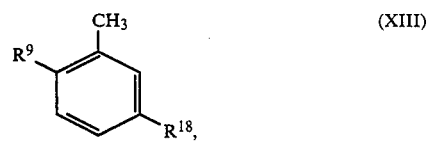

in which $R^9$ has the meaning mentioned and $R^{18}$ denotes alkyl or aryl.

The smoothness and selectivity of the process according to the invention is surprising and could in no way have been predicted by knowledge of the state of the art, since it was to be presumed that the phenylmethane derivatives undergo no reaction with a tert.-alkyl group in the presence of an aromatic hydrocarbon and of a Friedel-Krafts catalyst or, under the influence of transbenzylation, lead to a non-uniform mixture in which the compound desired is obtained either in only low amounts or from which it could only be isolated with difficulty, at least with losses of yield and with high costs.

The 2-benzyl-toluenes which can be prepared according to the invention are intermediates, such as for the preparation of valuable dyestuffs, for example in the case where one of the ortho positions to the methylene group is unsubstituted in the aromatic nucleus A of (I), and for the preparation of anthraquinone dyestuffs via the pertinent anthracenes and anthraquinones (EP-OS (European Published Specification) No. 37,628).

EXAMPLE 1

52.8 g (0.2 mol) of 2-benzyl-4-tert.-butyl-toluene (89.9% purity), 184.3 g (2.0 mol) of dry toluene and 8.11 g (0.05 mol) of iron-(III) chloride (anhydrous, sublime) were placed in a stirring apparatus, provided with stirrer, reflux condenser and thermometer. The mixture was heated for 6 h at 50° C. with stirring and cooled, 250 ml of water were added to the reaction mixture, and the aqueous phase was separated from the organic phase after thorough mixing. The aqueous phase was extracted once with 300 ml of methylene chloride, and the organic phases were each washed once with 100 ml of 10% strength aqueous hydrochloric acid and twice with 100 ml of water in each case. After drying the combined organic phases over sodium sulphate, the readily volatile components were stripped off on a rotary separator. The residue weighed 65.8 g and contained 47.6% = 31.3 g of 2-benzyl-toluene according to gas chromatographic analysis. The crude yield was, thus, 86% of the theoretical yield.

The reaction mixture was fractionated with the aid of a 30 cm Vigreux column in vacuo. After a first running of 15.41 g, 5.8 g of an intermediate fraction which consisted, to 52.9%, of 2-benzyl-toluene according to gas chromatographic anatysis were obtained at a temperature of 40°-94° C./1.2 mbar. The main fraction passed over entirely at 95°-99° C./1.2 mbar (24.73 g. 97.5% purity according to gas chromatographic analysis). A final running could subsequently be obtained at 99°-123° C./1.2 mbar (7.75 g, 38.1% purity according to gas chromatographic analysis.

The distilled yield, calculated over all the fractions, was 83% of the theoretical yield, and 66% of the theoretical yield calculated on the main fraction.

The 2-benzyl-toluene obtained was identified by nuclear magnetic resonance spectroscopy, by infrared spectroscopy and by mass spectroscopy, and was recognized as being identical to a sample which had been prepared from 2-methylbenzyl chloride and benzene.

EXAMPLE 2

(Comparison example)

2.37 g (9 mmol) of 2-benzyl-4-tert.-butyl-toluene (90% purity) and 9.21 g (100 mmol) of toluene were placed, dried, in a flask, fitted with magnetic stirrer and reflux condenser. 0.95 g (5 mmol) of $TiCl_4$ were added and the mixture stirred for 6 h at 50° C. According to a gas chromatographic analysis, no reaction occurred.

EXAMPLE 3

(Comparison example)

The procedure as in Example 2 was carried out, but at 100° C. According to gas chromatographic analysis, no reaction occurred.

EXAMPLE 4

2.37 g (9 mmol) of 2-benzyl-4-tert.-butyl-toluene (90% purity) and 7.81 g (100 mmol) of dry benzene were placed in a flask fitted with magnetic stirrer and reflux condenser. 0.811 g of dry, sublimed iron-(III) chloride was added and the mixture stirred for 6 h at 50° C. According to gas chromatographic analysis, a crude yield of 82% of the theoretical yield was obtained.

EXAMPLES 5-7

The dependency of the reaction on the amount of catalyst is shown in Examples 5-7.

General procedure: 2.37 g (9 mmol) of 2-benzyl-4-tert.-butyl-toluene (90% purity) and 9.21 g (100 mmol) of dry toluene were weighed into a flask. Iron-(III) chloride was added and the mixture stirred for 6 h at 50° C. The reaction mixture was then examined by gas chromatography. The results are listed in Table 1.

TABLE 1

| Iron-(III) chloride | | Yield | Yield relative to conversion [% of theory] |
|---|---|---|---|
| [g] | [mmol] | [% of theory] | |
| 0.162 | 1 | 39 | 89 |
| 0.324 | 2 | 92 | 99 |
| 0.811 | 5 | 82 | 91 |

EXAMPLE 8

111.05 g (0.36 mol) of 2-(2'-chloro-benzyl)-4-tert.-butyl-toluene (89% purity), 334.5 g (3.63 mol) of dry toluene and 29.44 g (0.18 mol) of anhydrous, sublimed iron-(III) chloride were placed in an apparatus as in Example 1. The mixture was stirred for 1.5 h at 50° C., cooled to room temperature and filtered, and the readily volatile components were stripped off on a rotary evaporator. The residue (143.5 g) was subjected to fractional distillation in vacuo over a 30 cm Vigreux column.

After a first running of 37.77 g, an intermediate fraction could be obtained at 42°-106° C. /0.4 mbar (5.78 g; 26.4% purity according to gas chromatographic analysis). The main running passed over uniformly at 106°-106.5° C./ 0.4 mbar (72.76 g, 94.9% purity according to gas chromatographic analysis). A further 6.9 g of product (53.6% purity according to gas chromatographic analysis) were obtained at 106.5° C.-130° C./0.4 mbar as a second running.

The distilled yield over all fractions was thus 94% of the theoretical yield; calculated on the main fraction, 88% of the theoretical yield could be isolated.

The 2-(2-chloro-benzyl)-toluene obtained was identified by nuclear magnetic resonance spectroscopy, by infra-red spectroscopy and by mass spectroscopy.

EXAMPLE 9

(Comparison example)

3.02 g (0.01 mol) of 2-(2-chlorobenyzl)-4-tert.-butyl-toluene (90.4% purity) and 7.81 g (0.1 mol) of dry benzene were placed in a flask, fitted with magnetic stirrer and reflux condenser. 0.7 g (0.005 mol) of $AlCl_3$ (95% purity) was added and the mixture stirred for 6 h at 50° C. The product mixture was analyzed by gas chromatography and mass spectroscopy. The following products were obtained:

Benzene—70.1%
Toluene—8.5%
tert.-Butyl-benzene—6.5%
Diphenyl-methane—7.4%
2-Benzyl-1-chloro-benzene—1.3%
2-(2-Chlorobenzyl-)-toluene—0.4% and also further compounds, which were not identified in more detail, in smaller amount.

EXAMPLE 10

300.6 g (2 mol) of p-tert.-butyl-toluene (98.7% purity) and 1.0 g (0.006 mol) of iron(III) chloride, anhydrous, sublimed, were placed in an apparatus as in Example 1, and the mixture was heated to 135° C. 33.2 g (0.2 mol) of o-chloro-benzyl chloride (97% purity) were metered in with stirring within 4 h, and the temperature was subsequently increased to 150° C. The mixture was stirred for 6 h at this temperature. After cooling, the excess p-tert.-butyl-toluene was removed by distillation in vacuo. 267.4 g of 99.5% pure tert.-butyl-toluene mixture, comprising 97.1% of p-tert.-butyl-toluene and 2.9% of m-tert.-butyl-toluene, corresponding to an amount of 89% of the batch=98% of the theoretical amount, were recovered.

184.3 g (2 mol) of dry toluene and 16.2 g (0.1 mol) of anhydrous, sublimed iron(III) chloride were added to the distillation bottom and the reaction mixture was stirred for 6 h at 50° C.

The reaction mixture was then filtered and subjected to a fractional distillation over a 20 cm Vigreux column.

154.5 g of toluene (99% purity) passed over as a first running at 30° C./20 mbar. 20.17 g of a 93% pure tert.-butyl-toluene mixture, comprising 65.1% of m-tert.-butyl-toluene and 34.9% of p-tert.-butyl-toluene, could be isolated as the 1st intermediate running at 31°-36° C./0.9 mbar.

The succeeding 2nd intermediate running, which passed over at 62°–118° C./1.5 mbar, produced 2.72 g (48.9% pure 2-(2-chloro-benzyl)-toluene according to gas chromatographic analysis). Finally, 32.15 g of (2(2-chlorobenzyl)toluene (92.8% purity) could be obtained at 118°–120° C./1.5 mbar. The distillative yield over all fractions was thus 72% of the theoretical yield, relative to 2-chlorobenzyl chloride.

EXAMPLE 11

3.49 g (10.00 mmol) of an isomeric mixture comprising 45% of 2-(2-chlorobenzyl)-4-tert.-butyl-toluene and 55% of 2-(2-chlorobenzyl)-5-tert.-butyltoluene (total content of both isomers in the charge material: 78%), 9.2 g (100.00 mmol) of toluene, dried, and 0.8 g (5.00 mmol) of anhydrous, sublimed iron(III) chloride were placed in a flask, fitted with magnetic stirrer and reflux condenser. The mixture was stirred for 6 h at 50° C. The mixture (13.5 g) was then cooled to room temperature and analyzed by gas chromatography. 15.7% of 2-(2-chlorobenzyl)toluene (corresponding to the theoretical yield) could be detected as the only diphenylmethane derivative.

EXAMPLE 12

3.68 g (40.00 mmol) of dry toluene, 1.298 g (8.00 mmol) of anhydrous iron(III) chloride and 6.04 g (22.02 mmol) of a 99.5% pure mixture of 2-(2-chlorobenzyl)-tert.-butyl-toluenes were placed in a flask, fitted with magnetic stirrer, reflux condenser and thermometer. The mixture was stirred for 6 h at 50° C. The reaction mixture was then poured onto ice water, the organic phase was separated, the aqueous phase was extracted once with 20 ml of toluene, and the organic phases were washed with water and 3% strength aqueous sodium bicarbonate solution and dried over $Na_2SO_4$.

After separation off of the solvent in a rotary evaporator, 8.15 g of a brownish oil remained which was 36.7% pure 2-(2-Chlorobenzyl)-toluene according to gas chromatographic analysis. The yield was thus 63% of the theoretical yield, relative to the mixture employed.

EXAMPLES 13 to 17

The dependency of the reaction on the temperature is represented in Examples 13–17 with reference to 2-(2-chlorobenzyl)-tert.-butyl-toluene mixtures.

General procedure 3.02 g (11.01 mmol) of a 99.5% pure mixture of 2-(2-chloro-benzyl)-tert.-butyl-toluenes, 9.21 g (100.000 mmol) of dry toluene and 0.162 g (1.00 mmol) of anhydrous iron(III) chloride were placed in a flask, fitted with magnetic stirrer, reflux condenser and thermometer. The mixture was stirred for 6 h at the appropriate temperature and then worked-up as described in Example 12. The yields, calculated after gas chromatographic analysis of the worked-up reaction mixture, are collated in Table 2.

TABLE 2

| Example | Temperature (°C.) | Yield (% of theory) |
|---|---|---|
| 13 | 0 | 7 |
| 14 | 24 | 57 |
| 15 | 50 | 46 |
| 16 | 80 | 17 |
| 17 | 110 | 16 |

EXAMPLE 18

92.14 g (1.0 mol) of dry toluene, 8.2 g (0.05 mol) of anhydrous iron(III) chloride and 38.3 g (0.11 mol) of a mixture of isomeric 2-(2,5-dichloro-benzyl)-tert.-butyl-toluenes, which additionally contained 5.5% of 2-(2,5-dichlorobenzyl)-toluene, were placed in an apparatus as in Example 1. The batch was warmed to 50° C. and stirred for 6 h at this temperature. The mixture was then filtered and the excess toluene was distilled in vacuo over a 30 cm Vigreux column. The residue (47.5 g) was fractionated in vacuo over a 20 cm Vigreux column.

11.87 g of a mixture of toluene, 3-tert.-butyl-toluene and 4-tert.-butyl-toluene passed over as a first running at 23°–82° C./0.7 mbar. 1.4 g of a colorless oil, which contained 62.6% of 2-(2,5-dichlorobenzyl)-toluene according to gas chromatographic analysis, were obtained in an intermediate running at 100°–125° C./0.6 mbar. The main cut distilled uniformly at 127°–131° C./0.6 mbar. 26.55 g of colorless oil could be obtained which comprised 90.5% of 2-(2,5-dichlorobenzyl)-toluene according to gas chromatographic analysis.

The distillative yield over all fractions is calculated as follows:

Distillate of intermediate fraction and main cut 100% pure product: 24.91 g minus product contained in the starting material: 2.11 g product produced during the reaction: 22.80 g 100% pure material corresponding to 83% of the theoretical yield, relative to the isomeric mixture employed.

EXAMPLE 19

25.94 g (0.08 mol) of 2-(4-nitrobenzyl)-4-tert.-butyl-toluene (90% purity, prepared by reaction of p-tert.-butyl-toluene with 4-nitro-benzyl chloride in the presence of $FeCl_3$ as catalyst, corresponding to Example 11, yield: 46% of theory distilled), 75.91 g (0.82 mol) of dry toluene and 6.68 g (0.04 mol) of anhydrous, sublimed iron(III) chloride were placed in an apparatus as in Example 1 and the reaction mixture was stirred for 6 h at 50° C. The mixture was then filtered and distilled in vacuo over a 20 -cm Vigreux column. After a first running of 6.44 g, an intermediate fraction was obtained at 80°–163° C./1.3 mbar.

(2.38 g, 75.5% of 2-(4-nitro-benzyl)-toluene according to gas chromatographic analysis). The main cut (6.85 g, 88.9% pure product) passed over at 163°–167° C./1.3 mbar.

A further 8.25 g of product (81.2% pure according to gas chromatographic analysis) were isolated in a subsequent fraction, passing over at 167° C./1.3 mbar. The distillative yield over all fractions was accordingly 14.59 g of 100% pure material (corresponds to 80% of the theoretical yield).

The compound obtained was identified by spectroscopic methods.

What is claimed is:

1. A process for the preparation of a 2-benzyl-toluene of the formula

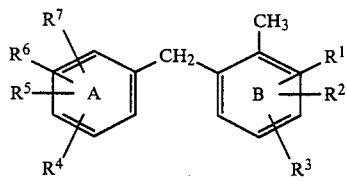

in which $R^1$ and $R^7$ independently of one another, denote hydrogen, halogen, alkyl, carbocyclic aryl, nitro, cyano, acylamino, carbocyclic aryloxy, carbocyclic aryl sulphonyl or alkylsulphonyl, where, in nucleus B, either the para position to the methyl group or the para position to the methylene group is unsubstituted and where two of the radicals $R^1$-$R^7$, when they are neighboring, can form a fused carbocyclic aromatic or cycloaliphatic ring, wherein 2-benzyl-tert.-alkyl-toluene of the formula

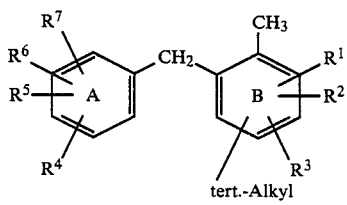

in which $R^1$ to $R^7$ have the meaning mentioned and the tert.-alkyl group is in the para position to the methyl group or in the para position to the methylene group, is reacted with an excess of an aromatic hydrocarbon of the formula

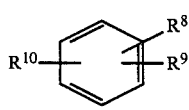

in which $R^8$ to $R^{10}$, independently of one another, denote hydrogen, alkyl or carbocyclic aryl, where two of the radicals $R^8$-$R^{10}$, when they are neighboring, can form a fused carbocyclic aromatic or cycloaliphatic ring, in the presence of anhydrous Fe-(III) halide wherein the reaction is carried out at 0°-150° C.

2. A process according to claim 1, wherein the 2-benzyl-tert.-alkyl-toulene is of the formula

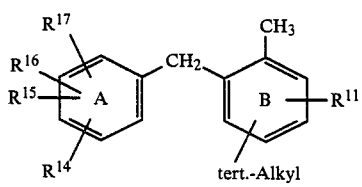

in which
$R^{11}$, and $R^{14}$ to $R^{17}$, independently of one another, denote hydrogen, fluorine, chlorine, bromine, nitro, alkyl or phenyl, where two of the radicals $R^{14}$-$R^{17}$, when they are neighboring, can form a fused carbocyclic aromatic or cycloaliphatic ring and the tert.-alkyl group is in the para position to the methyl group or in the para position to the methylene group.

3. A process according to claim 1, wherein the 2-benzyl-tert.-alkyl-toulene is of the formula

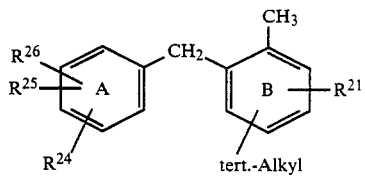

in which
$R^{21}$ denotes hydrogen or alkyl, and
$R^{24}$, $R^{25}$ and $R^{26}$, independently of one another, denote hydrogen, fluorine, chlorine, bromine, nitro, alkyl or phenyl, where two of the radicals $R^{24}$, $R^{25}$ and $R^{26}$, when they are neighboring, can form a fused carbocyclic aromatic or cycloaliphatic ring.

4. A process according to claim 1, wherein the aromatic hydrocarbon is of the formula

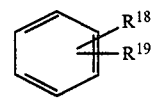

in which $R^{18}$ and $R^{19}$, independently of one another, denote hydrogen, alkyl or aryl and, in the case where they are neighboring, can also form a fused carbocyclic aromatic or cycloaliphatic ring.

5. A process according to claim 1, wherein 0.1–1 mol of anhydrous iron-(III) halide is employed per mol of 2-benzyl-tert.-alkyl-toulene.

6. A process according to claim 1, wherein 2–20 mol of the aromatic hydrocarbon is employed per mol of 2-benyl-tert.-alkyl-toulene.

7. A process according to claim 1, wherein the reaction is carried out at 20°-150° C.

8. A process for the preparation of a 2-benzyl-toulene of the formula

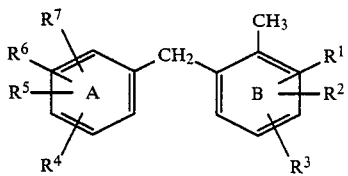

in which $R^1$ to $R^7$, independently of one another, denote hydrogen, halogen, alkyl, carbocyclic aryl, nitro, cyano, acylamino, carbocyclic aryloxy, carbocyclic arylsulphonyl or alkyl sulphonyl, where, in nucleus B, either the para position to the methyl group or the para position to the methylene group is unsubstituted and where two of the radicals $R^1$-$R^7$, when they are neighboring, can form a fused carbocyclic aromatic or cycloaliphatic ring, wherein, in a first stage, a benzyl halide of the formula

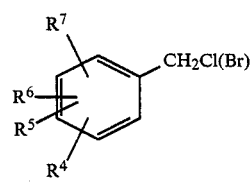

in which $R^4$ to $R^7$ have the meaning mentioned, is reacted with excess tert.-alkyl-toulene of the formula

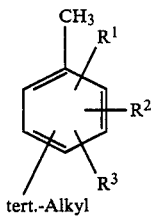

in which $R^1$ to $R^3$ have the meaning mentioned, an ortho position to the methyl group is free and the tert.-alkyl group is in the para position to the methyl group or to the free ortho position mentioned, at elevated temperature in the presence of anhydrous iron-(III) halide, and, in a second stage, the reaction mixture obtained is reacted with an aromatic hydrocarbon of the formula

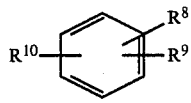

$R^8$ to $R^{10}$, independently of one another, denote hydrogen, alkyl or aryl, where two of the radicals $R^8$–$R^{10}$, when they are neighboring, can form a fused carbocyclic aromatic or cycloaliphatic ring.

9. A process according to claim 8, wherein the unreacted excess of the tert.-alkyl-toulene is removed by distillation before carrying out the second stage.

10. A process according to claim 8, wherein a toulene of the formula

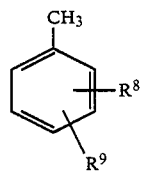

in which $R^8$ and $R^9$, independently of one another, denote hydrogen, alkyl or carbocyclic aryl, and, in the case where they are neighboring, can also form a fused carbocyclic aromatic or cycloaliphatic ring, and in which one of the ortho positions to the methyl group is free and the para position to the methyl group or to the free ortho position mentioned is likewise free, is employed as aromatic hydrocarbon, and the tert.-alkyl-toluene of the formula

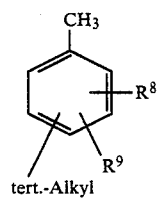

in which $R^8$ and $R^9$ have the meaning mentioned and in which one of the ortho positions to the methyl group is free and the tert.-alkyl group is in the para position to the methyl group or to the free ortho position mentioned, produced from this toluene in the course of the reaction is isolated and re-reacted, in the first stage, with a benzyl halide.

11. A process according to claim 1, wherein the reaction is carried out at 0°–100° C.

12. A process according to claim 1, wherein the reaction is carried out at 5°–80° C.

* * * * *